(12) United States Patent
Jois et al.

(10) Patent No.: US 8,779,224 B2
(45) Date of Patent: Jul. 15, 2014

(54) PROCESS FOR THE PRODUCTION OF GASOLINE BLENDING COMPONENTS AND AROMATIC HYDROCARBONS FROM LOWER ALKANES

(75) Inventors: Yajnanarayana Halmuthur Jois, Katy, TX (US); Ann Marie Lauritzen, Houston, TX (US); Ajay Madhav Madgavkar, Katy, TX (US)

(73) Assignee: Shell Oil Company, Houston, TX (US)

( * ) Notice: Subject to any disclaimer, the term of this patent is extended or adjusted under 35 U.S.C. 154(b) by 332 days.

(21) Appl. No.: 13/082,756

(22) Filed: Apr. 8, 2011

(65) Prior Publication Data

US 2011/0251444 A1    Oct. 13, 2011

Related U.S. Application Data

(60) Provisional application No. 61/323,017, filed on Apr. 12, 2010.

(51) Int. Cl.
*C10L 1/06* (2006.01)
*C10L 1/16* (2006.01)
*C07C 13/465* (2006.01)

(52) U.S. Cl.
USPC ............... 585/24; 585/14; 585/25; 585/26; 585/27; 44/300

(58) Field of Classification Search
CPC ... C10L 1/1608; C10L 1/06; C10L 2270/023; C07C 13/465
USPC ............ 585/415–421, 483–489, 24–27
See application file for complete search history.

(56) References Cited

U.S. PATENT DOCUMENTS

| | | | | |
|---|---|---|---|---|
| 3,996,305 | A * | 12/1976 | Berger | 585/474 |
| 4,041,091 | A * | 8/1977 | Henry | 585/470 |
| 4,350,835 | A * | 9/1982 | Chester et al. | 585/415 |
| 4,565,897 | A * | 1/1986 | Gane et al. | 585/415 |
| 4,746,763 | A * | 5/1988 | Kocal | 585/417 |
| 4,795,844 | A * | 1/1989 | Martindale et al. | 585/415 |
| 4,806,699 | A * | 2/1989 | Smith et al. | 585/314 |
| 4,806,700 | A * | 2/1989 | Martindale | 585/322 |

(Continued)

FOREIGN PATENT DOCUMENTS

| | | | |
|---|---|---|---|
| EP | 0244162 | 11/1987 | C07C 2/76 |
| WO | WO2009105447 | 8/2009 | B01J 29/064 |

OTHER PUBLICATIONS

U.S. Appl. No. 61/257,085, entitled Process for the Conversion Mixed Lower Alkanes to Aromatic Hydrocarbons, filed Nov. 2, 2009.

(Continued)

*Primary Examiner* — Ellen McAvoy

(57) ABSTRACT

An integrated process for producing gasoline blending components and aromatic hydrocarbons which comprises: (a) contacting a lower alkane feed with an aromatic hydrocarbon conversion catalyst to produce an aromatic reaction product mixture which is comprised of benzene and/or toluene and/or xylene, $C_9$ aromatic products, $C_{10}$ aromatic products including naphthalene and, optionally, $C_{11+}$ aromatic products, (b) separating and recovering the aromatic reaction product mixture, (c) separating and recovering benzene, (d) optionally separating recovering toluene and/or xylene, and (e) separating and recovering the $C_9$ aromatic products and the $C_{10}$ aromatic products which boil at a lower temperature than naphthalene from the naphthalene and the $C_{10}$ aromatic reaction products which boil at a higher temperature than naphthalene and any $C_{11+}$ aromatic products.

2 Claims, 3 Drawing Sheets

(56) References Cited

U.S. PATENT DOCUMENTS

| | | | |
|---|---|---|---|
| 4,855,522 A * | 8/1989 | Diaz | 585/417 |
| 4,857,498 A | 8/1989 | Dejaifve et al. | 502/304 |
| 4,899,006 A * | 2/1990 | Dave et al. | 585/415 |
| 5,138,112 A * | 8/1992 | Gosling et al. | 585/317 |
| 5,227,557 A | 7/1993 | Bournonville et al. | 585/419 |
| 5,278,344 A * | 1/1994 | Gosling et al. | 585/322 |
| 5,685,972 A * | 11/1997 | Timken et al. | 208/89 |
| 6,353,143 B1 | 3/2002 | Fang et al. | 585/1 |
| 7,186,871 B2 * | 3/2007 | Mitchell et al. | 585/418 |
| 7,186,872 B2 * | 3/2007 | Juttu et al. | 585/419 |
| 7,276,636 B2 | 10/2007 | Jeanneret | 585/323 |
| 7,563,358 B2 * | 7/2009 | Stavens et al. | 208/138 |
| 2005/0258076 A1 * | 11/2005 | Houzvicka | 208/134 |
| 2008/0051615 A1 | 2/2008 | Stavens et al. | 585/266 |
| 2009/0156870 A1 | 6/2009 | Lauritzen et al. | 585/24 |
| 2009/0209794 A1 | 8/2009 | Lauritzen et al. | 585/415 |
| 2009/0209795 A1 | 8/2009 | Lauritzen et al. | 585/417 |

OTHER PUBLICATIONS

U.S. Appl. No. 61/257,149, entitled Process for the Conversion Lower Alkanes to Aromatic Hydrocarbons, filed Nov. 2, 2009.

* cited by examiner

PROCESS FOR THE PRODUCTION OF GASOLINE BLENDING COMPONENTS AND AROMATIC HYDROCARBONS FROM LOWER ALKANES

This application claims priority to U.S. Provisional Application No. 61/323,017, filed on Apr. 12, 2010, which is herein incorporated by reference.

FIELD OF THE INVENTION

The present invention relates to a process for producing gasoline blending components and aromatic hydrocarbons from lower alkanes. The invention also relates to a novel gasoline blending component.

BACKGROUND OF THE INVENTION

There is a projected global shortage for benzene which is generally obtained, along with other aromatic hydrocarbons, by separating a feedstock fraction which is rich in aromatic compounds, such as reformate produced through a catalytic reforming process and pyrolysis gasolines produced through a naphtha cracking process, from non-aromatic hydrocarbons using a solvent extraction process. To meet this projected supply shortage, numerous catalysts and processes for on-purpose production of aromatics (including benzene) from alkanes containing six or less carbon atoms per molecule have been investigated. For example, U.S. Pat. No. 4,350,835 describes a process for converting ethane-containing gaseous feeds to aromatics using a crystalline zeolite catalyst of the ZSM-5-type family containing a minor amount of Ga. As another example, U.S. Pat. No. 7,186,871 describes aromatization of $C_1$-$C_4$ alkanes using a catalyst containing Pt and ZSM-5.

It is well known to add certain blending components to gasolines to improve the properties thereof such as the RON or the MON. Commonly used blending components include naphthas (e.g., straight-run gasoline, alkylate, reformate, toluene, xylene), cracked gasoline, pyrolysis gasoline, and paraffinic hydrocarbons.

U.S. Pat. No. 6,353,143 describes fuel compositions which are comprised of a branched hydrocarbon, such as an isoparaffin, and an aromatic hydrocarbon. An example of a suitable aromatic hydrocarbon given is AROMATIC 150 Fluid from Exxon Chemical which typically is composed of a narrow-cut aromatic solvent containing about 23 wt. % tetra-methyl benzenes, about 22 wt. % ethyl dimethyl benzenes, about 15 wt. % mono-, di- and tri-methyl indanes, about 8 wt. % diethyl benzenes, about 8 wt. % naphthalene, about 5 wt. % trimethyl benzenes, about 2 wt. % indane, and about 1 wt. % or less of methyl ethyl benzenes, propyl benzenes, methyl propyl benzenes, butyl benzenes, hexyl benzenes, indene, methyl naphthalenes, and xylenes. Another example of an aromatic hydrocarbon given is AROMATIC 100 which typically is composed of a narrow-cut aromatic solvent containing about 40 wt. % trimethyl benzenes, about 35 wt. % methyl ethyl benzenes, about 1 wt. % propyl and isopropyl benzenes, about 3 wt. % ethyl dimethyl benzenes, about 2 wt. % methyl (n- and iso-) propyl benzenes, about 2 wt. % diethyl benzenes, less than about 1 wt. % each of mono butyl benzenes and tetramethyl benzenes, about 6 wt. % xylenes, and minor amounts of ethyl benzene and $C_{10}$-$C_{11}$ saturates.

SUMMARY OF THE INVENTION

The present invention provides an integrated process for producing gasoline blending components and aromatic hydrocarbons which comprises:

(a) contacting a lower alkane feed with an aromatic hydrocarbon conversion catalyst to produce an aromatic reaction product mixture which is comprised of benzene and/or toluene and/or xylene, $C_9$ aromatic products, $C_{10}$ aromatic products including naphthalene and, optionally, $C_{11+}$ aromatic products, (b) separating and recovering the aromatic reaction product mixture, (c) separating and recovering benzene, and (d) separating and recovering toluene and/or xylene and the $C_9$ aromatic products and the $C_{10}$ aromatic products which boil at a lower temperature than naphthalene from the naphthalene and the $C_{10}$ aromatic reaction products which boil at a higher temperature than naphthalene and any $C_{11+}$ aromatic products.

DETAILED DESCRIPTION OF THE INVENTION

Figure 1:
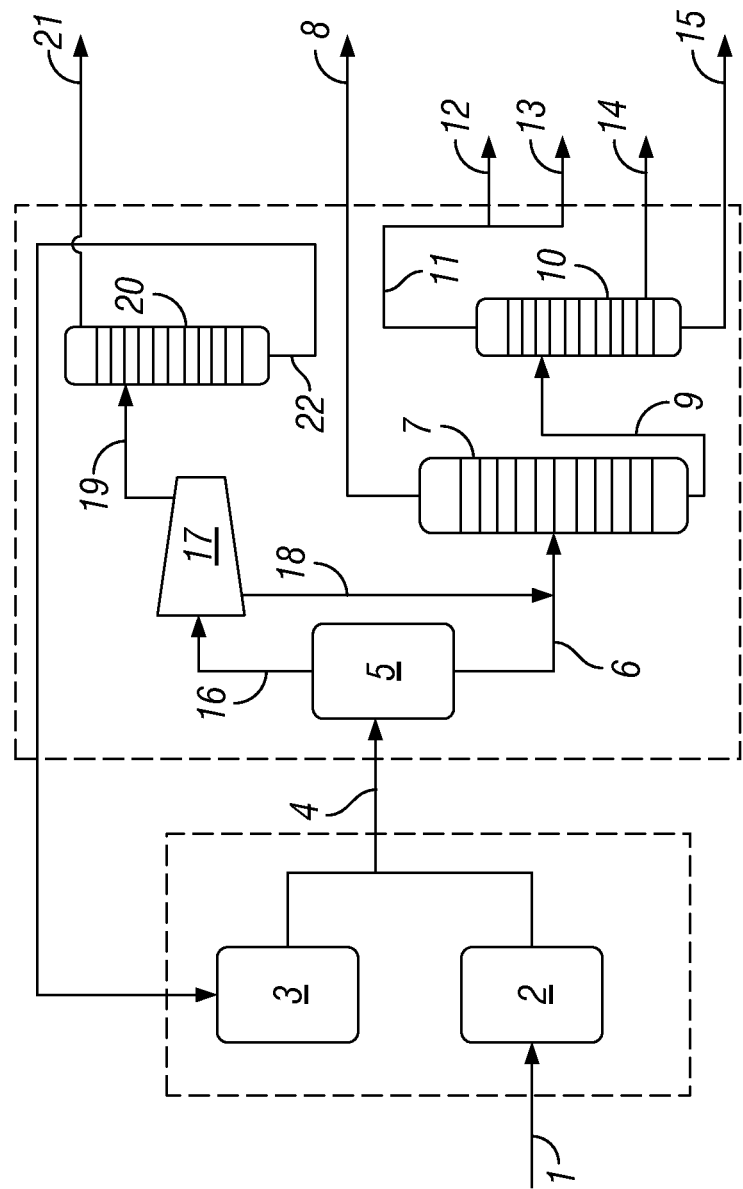
FIG. 1 is a flow diagram of a two stage aromatization process wherein benzene, toluene and/or xylene and the $C_{9-10}$ fraction are recovered separately.

Gasolines typically comprise mixtures of hydrocarbons boiling in the range from 25 to 230° C. (EN-ISO 3405), the optimal ranges and distillation curves typically varying according to climate and season of the year. The hydrocarbons in a gasoline may be derived by any means known in the art, conveniently the hydrocarbons may be derived in any known manner from straight-run gasoline, synthetically-produced aromatic hydrocarbon mixtures, thermally or catalytically cracked hydrocarbons, hydro-cracked petroleum fractions, catalytically reformed hydrocarbons or mixtures of these.

The specific distillation curve, hydrocarbon composition, research octane number (RON) and motor octane number (MON) of the gasoline are not critical. Conveniently, the research octane number (RON) of the gasoline may be at least 80, for instance in the range of from 80 to 110 (EN 25164). The motor octane number (MON) of the gasoline may conveniently be at least 70, for instance in the range of from 70 to 110 (EN 25163).

Gasoline is composed of many different hydrocarbons. Typically, gasoline comprises components selected from one or more of the following groups; saturated hydrocarbons, olefinic hydrocarbons, aromatic hydrocarbons, and oxygenated hydrocarbons. Typically, the aromatic hydrocarbon content of the gasoline may be in the range of from 0 to 70 percent by volume based on the gasoline (ASTM D1319).

Crude oil enters a refinery and is processed through various units before being blended into gasoline. A refinery may have a fluid catalytic cracker (FCC), an alkylate unit, and a reformer, each of which produces gasoline blending components. Alkylate gasoline, for example, is valuable because it has a very high octane, and can be used to produce high-octane (and higher value) blends. Light straight run gasoline is the least processed stream. It is cheap to produce, but it has a low octane. The person specifying the gasoline blends has to mix all of the components together to meet the product specifications.

It is well known to add certain blending components to gasoline to improve the properties thereof such as the RON or the MON. Commonly used blending components include naphthas (e.g., straight-run gasoline, alkylate, reformate, benzene, toluene, xylene), cracked gasoline, pyrolysis gasoline, and paraffinic hydrocarbons. The present invention provides a novel gasoline blending component which comprises from about 1 to 10 wt % indane, from about 40 to 60% wt indene, from about 4 to 20 wt % $C_9$ aromatics other than indane or indene, and from about 25 to 35 wt % $C_{10}$ aromatics other than naphthalene.

The process of the present invention comprises bringing into contact a hydrocarbon feedstock containing lower alkanes, and possibly other hydrocarbons, and a catalyst composition suitable for promoting the reaction of such hydrocarbons to aromatic hydrocarbons, such as benzene, at a temperature from about 400 to about 700° C. and a pressure from about 0.01 to about 1.0 Mpa absolute. The gas hourly space velocity (GHSV) per hour may range from about 300 to about 6000. The process may be carried out in a single stage or in multiple, preferably two, stages. If a two-stage process is used, the conditions in each stage may fall in the above ranges and may be the same or different.

Suitable feed streams for use herein include alkane streams which may contain primarily one or more $C_2$, $C_3$, and/or $C_4$ alkanes (referred to herein as "lower alkanes"), for example an ethane/propane/butane-rich stream derived from natural gas, refinery or petrochemical streams including waste streams. Examples of potentially suitable feed streams include (but are not limited to) residual ethane and propane from natural gas (methane) purification, pure ethane, propane and butane streams (also known as Natural Gas Liquids) co-produced at a liquefied natural gas site, $C_2$-$C_5$ streams from associated gases co-produced with crude oil production, unreacted ethane "waste" streams from steam crackers, and the $C_1$-$C_3$ byproduct stream from naphtha reformers. The lower alkane feed may be deliberately diluted with relatively inert gases such as nitrogen and/or with various light hydrocarbons and/or with low levels of additives needed to improve catalyst performance.

In one embodiment, the majority of the feedstock is comprised of ethane and propane. In another embodiment, the feedstock is comprised of mixed $C_2$-$C_4$ alkanes. In still another embodiment, the feedstock is comprised of primarily propane and butane. The feedstock may contain in addition other open chain hydrocarbons containing between 3 and 8 carbon atoms as coreactants. Specific examples of such additional coreactants are propylene, isobutane, n-butenes and isobutene. The feed may contain up to about 20 weight percent of $C_2$-$C_4$ olefins, preferably no more than about 10 weight percent olefins. Too much olefin content may cause an unacceptable amount of coking. The hydrocarbon feedstock preferably may be comprised of at least about 30 percent by weight of $C_{2-4}$ hydrocarbons, preferably at least about 50 percent by weight.

In one embodiment, the lower alkane feed is comprised of at least propane and ethane and the process is carried out in two stages as described in copending, commonly assigned provisional U.S. patent application No. 61/257,085, entitled PROCESS FOR THE CONVERSION MIXED LOWER ALKANES TO AROMATIC HYDROCARBONS, filed Nov. 2, 2009, which is herein incorporated by reference in its entirety. In the first stage, the reaction conditions may be optimized for the conversion of propane to benzene. In the second stage, reaction conditions may be optimized for the conversion of ethane to benzene. Optionally, the second stage reaction conditions may also be optimized for the conversion to BTX of any other non-aromatic hydrocarbons which may be produced in the first stage.

In another embodiment, as described in copending, commonly assigned provisional U.S. patent application No. 61/257,149, entitled PROCESS FOR THE CONVERSION LOWER ALKANES TO AROMATIC HYDROCARBONS, filed Nov. 2, 2009, which is herein incorporated by reference in its entirety, the process (a) comprises alternately contacting the lower alkane feed with an aromatization catalyst in a reactor for a short period of time, preferably 10 minutes or less, and then contacting the aromatization catalyst with hydrogen at elevated temperature for a short period of time, preferably 20 minutes or less, (b) repeating the cycle of step (a) at least one time, (c) regenerating the aromatization catalyst by contacting it with an oxygen-containing gas at elevated temperature, and (d) repeating steps (a) through (c) at least one time.

One important advantage of the aromatization process used herein is that little or no $C_{5+}$ non-aromatic hydrocarbons are produced. The $C_{1-4}$ non-aromatic hydrocarbons which are produced may be recycled or used for fuel, etc. The major products produced are aromatic. Benzene, and generally toluene and xylene, are recovered, leaving a substantial amount of $C_{9+}$ aromatic hydrocarbons. We have discovered that a significant portion of the $C_{9+}$ fraction produced from lower alkanes in this aromatization process may be used as a gasoline-blending component with attractive properties. Accordingly, a product separation scheme is incorporated in the aromatization process to efficiently separate and recover the desirable portion of the $C_{9+}$ mixture so that a maximum amount of desirable gasoline blending component is obtained. The $C_{9+}$ fraction includes naphthalene and higher boiling $C_{10+}$ aromatic hydrocarbons which are not useful for gasoline blending components because its boiling range is higher than specified/typical gasoline range.

In the present invention, the $C_9$ aromatic hydrocarbons and the $C_{10}$ aromatic hydrocarbons which boil at lower temperatures than naphthalene are recovered separately. The $C_9$ aromatic hydrocarbons include indane, indene, durene, propylbenzene, etc. and the lower boiling $C_{10}$ aromatic hydrocarbons include methylindane, methylindene, methylpropylbenzene, butylbenzene, diethylbenzene, etc. The combined $C_9$ aromatic hydrocarbons and $C_{10}$ aromatic hydrocarbons which boil at lower temperatures than naphthalene comprise the gasoline blending component of the present invention. It may comprise from about 1 to 10 wt % indane, from about 40 to 60 wt % indene, from about 4 to 20 wt % $C_9$ aromatics other than indane or indene, and from about 25 to 35 wt % $C_{10}$ aromatics other than naphthalene.

Indane is a hydrocarbon petrochemical compound with chemical formula $C_9H_{10}$. Derivatives include compounds such as 1-methyl-indane and 2-methyl-indane (where one methyl group is attached to the five carbon ring), 4-methyl-indane and 5-methyl-indane (where one methyl group is attached to the benzene ring), various dimethyl-indanes, and various pharmaceutical derivatives. Indene is an unsaturated polycyclic hydrocarbon with chemical formula $C_9H_8$. It is composed of a benzene ring fused with a cyclopentene ring.

Multiple chemical analyses of the $C_{9+}$ fraction obtained experimentally show that indane and indene form the majority of the $C_9$ molecules while methyl substituted indane and indene and naphthalene form the majority of the $C_{10}$ molecules. Indane and indene

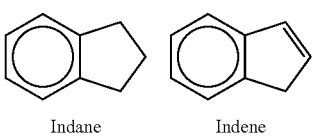

Indane   Indene are similar in structure to benzene, ethyl benzene and propyl benzene which are known to have high octane and high flame speed boosting properties as shown in Table 1.

TABLE 1

| Compound | RON | MON | Flame Speed cm/sec | b.p. ° C. |
|---|---|---|---|---|
| Benzene | 105 | 99 | 84 | 80.1 |
| Toluene | 120 | 109 | 67.9 | 110.6 |
| Isooctane | 100 | 100 | 67 | 98.5 |
| Ethylbenzene | 111.2 | 97.9 | 76.9 | 136.2 |
| 1,2,4 Trimethylbenzene (Pseudocumene) | 110.5 | 105.8 | 58.3 | 169.4 |
| 1,3,5 Trimethylbenzene (Mesitylene) | 120.3 | 120.3 | 56 | 164.7 |
| isopropylbenzene | 113.1 | 99.3 | 76.3 | 152.4 |
| n-propylbenzene | | | | 74.1 |
| t-butylbenzene | | | | 75.7 |

FIG. 1 is a flow diagram of a two stage aromatization process wherein a $C_{9-10}$ only fraction is recovered. Lower alkane feed enters stage 1 aromatization reactor 2 through line 1. The reaction products are combined with the reaction products from stage 2 aromatization reactor 3 in line 4 which is conveyed to a vapor-liquid separator 5. The liquid bottoms leave the separator 5 in line 6 and are conveyed to the debenzenizer 7 wherein benzene is separated from the other aromatic products and is recovered in line 8. The other aromatic products in the bottom stream 9 are conveyed to the toluene-xylene-$C_{9-10}$ separation stage 10. The toluene and xylene leave separation stage 10 through line 11 and are recovered separately as toluene in line 12 and xylene in line 13. The $C_{9-10}$ fraction is taken out of separation stage 10 and recovered in line 14. The remaining $C_{9-10}$, aromatics leave stage 10 through line 15.

Vapor stream 16 leaves separator 5 and is compressed in compressor 17. Any aromatics carried over to the compressor are conveyed to the debenzenizer 7 through line 18. The other liquids are conveyed through line 19 to demethanizer 20 wherein the methane and hydrogen are separated and recovered as fuel gas in line 21. The bottom stream 22 of the demethanizer 20 contains $C_{2-4}$ hydrocarbons which are recycled to the second stage aromatization reactor 3.

Figure 2:
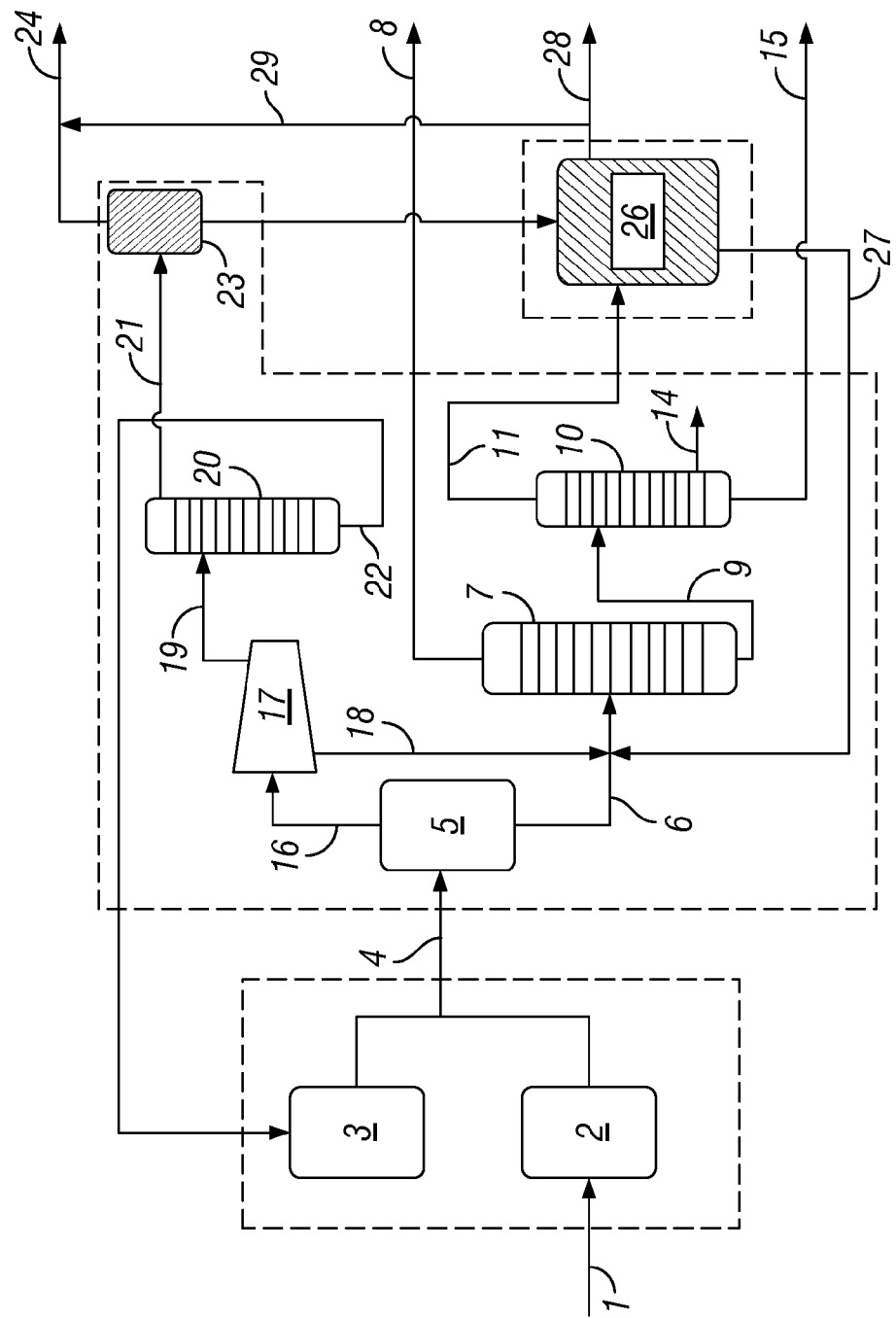
FIG. 2 is a flow diagram of a two stage aromatization process wherein the process also comprises hydrodealkylation of the toluene and xylene to make additional benzene.

FIG. 2 is a flow diagram of the two stage aromatization process wherein the process scheme of FIG. 1 includes at the end a hydrodealkylation section wherein the toluene and xylene are reacted to produce more benzene. Most of the process description is the same as for FIG. 1. Instead of being separated, the toluene and xylene in line 11 are conveyed to a hydrodealkylation unit 26 which produces additional benzene in line 28 and some fuel gas components in line 29. Unreacted toluene and xylene are recycled to the debenzenizer through line 27. The overhead stream 21 from demethanizer 20 is conveyed to separator 23 which separates hydrogen from other fuel gas components. The hydrogen is conveyed through line 25 to the hydrodealkylation unit 26. The remaining fuel gas components from separator 23 are combined with line 29 and recovered as fuel gas through line 24.

Figure 3:
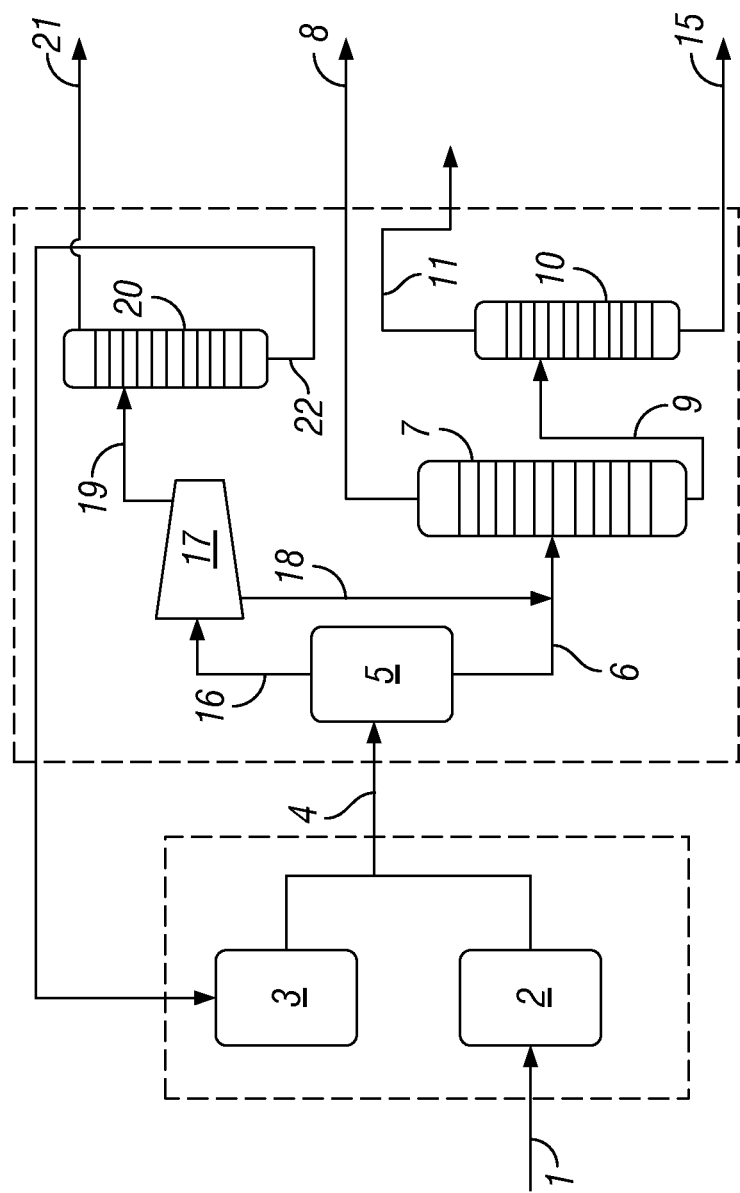
FIG. 3 is a flow diagram of the two stage aromatization process wherein the $C_{9-10}$ fraction is recovered together with the toluene and xylene as a single gasoline blending component.

FIG. 3 is a flow diagram of a two stage aromatization process wherein the $C_{9-10}$ fraction is recovered together with the toluene and xylene as a single gasoline blending component. In this embodiment, the toluene, xylene and the $C_{9-10}$ fractions are not recovered separately but are recovered together as a combined gasoline blending component in line 11.

Any one of a variety of catalysts may be used to promote the reaction of the lower alkanes to aromatic hydrocarbons. One such catalyst is described in U.S. Pat. No. 4,899,006 which is herein incorporated by reference in its entirety. The catalyst composition described therein comprises an aluminosilicate having gallium deposited thereon and/or an aluminosilicate in which cations have been exchanged with gallium ions. The molar ratio of silica to alumina is at least 5:1.

Another catalyst which may be used in the process of the present invention is described in EP 0 244 162. This catalyst comprises the catalyst described in the preceding paragraph and a Group VIII metal selected from rhodium and platinum. The aluminosilicates are said to preferably be MFI or MEL type structures and may be ZSM-5, ZSM-8, ZSM-11, ZSM-12 or ZSM-35.

Other catalysts which may be used in the process of the present invention are described in U.S. Pat. No. 7,186,871 and U.S. Pat. No. 7,186,872, both of which are herein incorporated by reference in their entirety. The first of these patents describes a platinum containing ZSM-5 crystalline zeolite synthesized by preparing the zeolite containing the aluminum and silicon in the framework, depositing platinum on the zeolite and calcining the zeolite. The second patent describes such a catalyst which contains gallium in the framework and is essentially aluminum-free.

Additional catalysts which may be used in the process of the present invention include those described in U.S. Pat. No. 5,227,557, hereby incorporated by reference in its entirety. These catalysts contain an MFI zeolite plus at least one noble metal from the platinum family and at least one additional metal chosen from the group consisting of tin, germanium, lead, and indium.

One preferred catalyst for use in this invention is described in U.S. Patent Application Publication No. 2009/0209795. This publication is hereby incorporated by reference in its entirety. This publication describes a catalyst comprising: (1) 0.005 to 0.1% wt (% by weight) platinum, based on the metal, preferably 0.01 to 0.05% wt, (2) an amount of an attenuating metal selected from the group consisting of tin, lead, and germanium, which is no more than 0.02% wt less than the amount of platinum, preferably not more than 0.2% wt of the catalyst, based on the metal; (3) 10 to 99.9% wt of an aluminosilicate, preferably a zeolite, based on the aluminosilicate, preferably 30 to 99.9% wt, preferably selected from the group consisting of ZSM-5, ZSM-11, ZSM-12, ZSM-23, or ZSM-35, preferably converted to the H+ form, preferably having a $SiO_2/Al_2O_3$ molar ratio of from 20:1 to 80:1, and (4) a binder, preferably selected from silica, alumina and mixtures thereof.

Another preferred catalyst for use in this invention is described in PCT Publication No. WO 2009/105447. This publication is hereby incorporated by reference in its entirety. The publication describes a catalyst comprising: (1) 0.005 to 0.1% wt (% by weight) platinum, based on the metal, preferably 0.01 to 0.06% wt, most preferably 0.01 to 0.05% wt, (2) an amount of iron which is equal to or greater than the amount of the platinum but not more than 0.50% wt of the catalyst, preferably not more than 0.20% wt of the catalyst, most preferably not more than 0.10% wt of the catalyst, based on the metal; (3) 10 to 99.9% wt of an aluminosilicate, preferably a zeolite, based on the aluminosilicate, preferably 30 to 99.9% wt, preferably selected from the group consisting of ZSM-5, ZSM-11, ZSM-12, ZSM-23, or ZSM-35, preferably converted to the H+ form, preferably having a $SiO_2/Al_2O_3$ molar ratio of from 20:1 to 80:1, and (4) a binder, preferably selected from silica, alumina and mixtures thereof.

Another preferred catalyst for use in this invention is described in U.S. Patent Application Publication No. 2009/0209794. This publication is hereby incorporated by reference in its entirety. This publication describes a catalyst comprising: (1) 0.005 to 0.1 wt % (% by weight) platinum, based on the metal, preferably 0.01 to 0.05% wt, most preferably 0.02 to 0.05% wt, (2) an amount of gallium which is equal to or greater than the amount of the platinum, preferably no more than 1 wt %, most preferably no more than 0.5 wt %, based on the metal; (3) 10 to 99.9 wt % of an aluminosilicate, preferably a zeolite, based on the aluminosilicate, preferably 30 to 99.9 wt %, preferably selected from the group consisting of ZSM-5, ZSM-11, ZSM-12, ZSM-23, or ZSM-35, preferably converted to the H+ form, preferably having a $SiO_2/Al_2O_3$ molar ratio of from 20:1 to 80:1, and (4) a binder, preferably selected from silica, alumina and mixtures thereof.

The unreacted methane and byproduct hydrocarbons may be used in other steps, stored and/or recycled. It may be necessary to cool these byproducts to liquefy them. When the ethane or mixed lower alkanes originate from an LNG plant as a result of the purification of the natural gas, at least some of these byproducts may be cooled and liquefied using the heat exchangers used to liquefy the purified natural gas (methane).

The toluene and xylene may be converted into benzene by hydrodealkylation. The hydrodealkylation reaction involves the reaction of toluene, xylenes, ethylbenzene, and higher aromatics with hydrogen to strip alkyl groups from the aromatic ring to produce additional benzene and light ends including methane and ethane which are separated from the benzene. This step substantially increases the overall yield of benzene and thus is highly advantageous.

Both thermal and catalytic hydrodealkylation processes are known in the art. Methods for hydrodealkylation are described in U.S. Patent Application Publication No. 2009/0156870 which is herein incorporated by reference in its entirety.

The integrated process of this invention may also include the reaction of benzene with propylene to produce cumene which may in turn be converted into phenol and/or acetone. The propylene may be produced separately in a propane dehydrogenation unit or may come from olefin cracker process vent streams or other sources. Methods for the reaction of benzene with propylene to produce cumene are described in U.S. Patent Application Publication No. 2009/0156870 which is herein incorporated by reference in its entirety.

The integrated process of this invention may also include the reaction of benzene with olefins such as ethylene. The ethylene may be produced separately in an ethane dehydrogenation unit or may come from olefin cracker process vent streams or other sources. Ethylbenzene is an organic chemical compound which is an aromatic hydrocarbon. Its major use is in the petrochemical industry as an intermediate compound for the production of styrene, which in turn is used for making polystyrene, a commonly used plastic material. Methods for the reaction of benzene with ethylene to produce ethylbenzene are described in U.S. Patent Application Publication No. 2009/0156870 which is herein incorporated by reference in its entirety.

Styrene may then be produced by dehydrogenating the ethylbenzene. One process for producing styrene is described in U.S. Pat. No. 4,857,498 which is herein incorporated by reference in its entirety. Another process for producing styrene is described in U.S. Pat. No. 7,276,636 which is herein incorporated by reference in its entirety.

EXAMPLES

The following examples are provided for illustrative purposes only and are not intended to limit the scope of the invention.

Example 1

Indane and indene were obtained from vendors. Toluene was used as a benchmark in this study of the fuel blending properties. The RON and MON of neat indane, indene, toluene, and a base fuel were tested using ASTM D-2699 and ASTM D-2700 test method. All compounds were tested in triplicate and the average of those results were presented in Table 2. The RON and MON of the base fuel and toluene were reasonably high as expected and the RON and MON of indane and indene were also reasonable high.

TABLE 2

| Density | Neat | Average | | | delta |
|---|---|---|---|---|---|
| g/ml | | RON | MON | R + M/2 | R − M |
| 0.743 | Base Fuel | 85.4 | 79.0 | 82.1 | 6.5 |
| 0.865 | Toluene | 114.5 | 106.0 | 110.3 | 8.5 |
| 0.965 | Indane | 100.7 | 85.5 | 93.1 | 15.2 |
| 0.996 | Indene | 108.0 | 98.5 | 103.2 | 9.5 |

The RON and MON of 1.2 v % indane and indene in base fuel blends were measured (see the top part of Table 3). The RON and MON of 3.7 v % toluene, 4.7 v % indane and 4.6 v % indene in base fuel blends were also measured (see the bottom part of Table 3). Table 3 below shows an increase in Research Octane Number of 0.43 and 0.5 with 1.2 v % of indane and indene, respectively. Table 3 shows an increase in Research Octane Number of 0.90 and 0.80 with 4.7 v % of indane and 4.6 v % indene, respectively.

TABLE 3

| Density (g/ml) | | Average | | | delta | | |
|---|---|---|---|---|---|---|---|
| | | RON | MON | R + M/2 | RON | MON | R + M/2 |
| 0.743 | Base Fuel (BF) | 86.3 | 79.8 | 83.0 | | | |
| 0.965 | Indane (1.2 v % in BF) | 86.7 | 79.8 | 83.2 | 0.43 | −0.03 | 0.2 |
| 0.996 | Indene (1.2 v %) | 86.8 | 79.5 | 83.1 | 0.50 | −0.30 | 0.1 |
| 0.743 | Base Fuel | 86.67 | 79.83 | 83.3 | | | |
| 0.865 | Toluene (3.7 v %) | 87.6 | 80.23 | 83.9 | 0.93 | 0.40 | 0.7 |
| 0.965 | Indane (4.7 v %) | 87.57 | 80.23 | 83.9 | 0.90 | 0.40 | 0.6 |
| 0.996 | Indene (4.6 v %) | 87.47 | 79.57 | 83.5 | 0.80 | −0.27 | 0.2 |

Such increase in octane number is known in the literature for aromatic molecules. However, it is generally compensated for by a decrease in flame speed. The flame speeds of above molecules were measured using the Leeds University bomb experiment technique at Leeds University facility. Fuel samples were tested under laminar conditions with initial conditions of 5 bar absolute pressure and 360K. All the burning velocities (flame speed) were measured at stoichiometric ratio of fuel to air. The experiments were conducted using the Leeds Mk2 fan stirred combustion vessel (Refer to www.engineering.leeds.ac.uk/mech for their facility). It is a stainless sphere of 30 liter volume with extensive optical access. The fuels were injected into the bomb and allowed to vaporize fully, then a stoichiometric amount of air was added. Content were heated to the desired temperature, mixed by stirring. Mixing fans were turned off prior to ignition. Pressure measured after 0.1 second of the ignition is recorded in Table 4. To determine if there was any significant change due to the presence of a component, it was decided to do experiments using 20 v % of the components in commercial grade gasoline. No significant change in flame speed was noted for indane or indene as shown in Table 4. The data in Tables 1-4 indicate that indane, indene, other $C_9$ aromatics, and certain $C_{10}$ aromatics other than naphthalene would comprise suitable gasoline blending components.

TABLE 4

Flame Speed Data

| Molecule | Blend Composition % in Gasoline | Flame Speed P/bar at 0.1 Second |
|---|---|---|
| Gasoline | 100 | 17.35 |
| Indane | 20 | 17.24 |
| Indene | 20 | 16.10 |

Example 2

Four runs were carried out in a lab-scale aromatization reactor at 0 kPag, 600° C. reactor wall temperature with repeated cycles of 10 minute exposure of the catalyst to feed followed by 20 minute exposure of the catalyst to hot hydrogen stripping. The feed and other conditions are described in Table 5 below. The catalysts used in these runs were prepared as described in U.S. Patent Application Publication No. 2009/02009794, which is incorporated by reference, with target metal loadings of 0.025 wt % platinum and 0.09 wt % gallium or 0.09 wt % platinum and 0.25 wt % gallium, on extrudates consisting of 80 wt % ZSM-5 CBV 2314 zeolite (available from Zeolyst International) and 20 wt % alumina binder. A gas chromatograph was used to provide quantitative analysis of the total product stream.

As shown in Table 5, the total $C_{9+}$ aromatics fraction accounted for about 8-15 wt % of the total aromatics product in runs conducted with all-ethane and mixed ethane/propane feeds. The $C_{9-10}$ aromatics fraction excluding naphthalene ranged between about 45 and 60% w of the total $C_{9+}$ aromatics product or about 4-8% w of the total aromatics product in these runs.

TABLE 5

| Run No. | 1 | 2 | 3 | 4 |
|---|---|---|---|---|
| Feed Composition | | | | |
| Ethane, % wt | 100 | 100 | 50 | 50 |
| Propane, % wt | -0- | -0- | 50 | 50 |
| Feed Rate, GHSV | 800 | 800 | 1000 | 1000 |
| Total Hrs on Feed | 14.4 | 50.7 | 27.2 | 50.7 |
| Avg Total C2 + C3 Conversion per Pass, % | 38.40 | 33.66 | 47.26 | 47.06 |
| Avg Total Arom. Yield per Pass, % wt | 23.57 | 20.01 | 30.19 | 32.81 |
| Avg C9+ Arom. Yield per Pass, % wt | 3.29 | 2.61 | 3.30 | 2.95 |
| Avg C9-C10 Arom. (Except Naphthalane) | | | | |
| Yield as % of C9+ Aromatics | 45.3 | 59.8 | 56.7 | 48.5 |
| Yield as % of Total Aromatics | 6.3 | 7.8 | 6.2 | 4.4 |
| Avg Naphthalene and Higher Aromatics | | | | |
| Yield as % of C9+ Aromatics | 54.7 | 40.2 | 43.3 | 51.5 |
| Yield as % of Total Aromatics | 7.6 | 5.2 | 4.7 | 4.6 |
| Final Boiling Point of Collected Liquid Product, ° C. | NA | 493 | NA | 453 |

What is claimed is:

1. A gasoline blending component which comprises from about 1 to 10 wt % indane, from about 40 to 60 wt % indene, from about 4 to 20 wt % C9 aromatics other than indane or indene, and from about 25 to 35 wt % C10 aromatics other than naphthalene.

2. A gasoline blending component as claimed in claim 1 which further comprises toluene and/or xylene.

* * * * *